United States Patent
Pichler et al.

(10) Patent No.: US 9,062,031 B2
(45) Date of Patent: Jun. 23, 2015

(54) METHOD OF PREPARING POLYMORPHIC PURE FORM A OF BAZEDOXIFENE ACETATE

(75) Inventors: Arthur Pichler, Kundl (AT); Andreas Hotter, Kundl (AT); Christoph Langes, Innsbruck (AT)

(73) Assignee: SANDOZ AG, Basel (CH)

( * ) Notice: Subject to any disclaimer, the term of this patent is extended or adjusted under 35 U.S.C. 154(b) by 19 days.

(21) Appl. No.: 13/976,216

(22) PCT Filed: Dec. 21, 2011

(86) PCT No.: PCT/EP2011/073669
§ 371 (c)(1),
(2), (4) Date: Aug. 14, 2013

(87) PCT Pub. No.: WO2012/089593
PCT Pub. Date: Jul. 5, 2012

(65) Prior Publication Data
US 2014/0294962 A1    Oct. 2, 2014

(30) Foreign Application Priority Data
Dec. 28, 2010  (EP) .................... 10197175

(51) Int. Cl.
*C07D 403/12*   (2006.01)
*C07D 209/12*   (2006.01)
(Continued)

(52) U.S. Cl.
CPC ............ *C07D 403/12* (2013.01); *A61K 31/404* (2013.01); *A61K 31/55* (2013.01); *C07D 209/12* (2013.01); *A61K 9/1617* (2013.01)

(58) Field of Classification Search
CPC ...... C07D 403/12; C07D 209/12; A61K 9/20; A61K 9/48; A61K 31/404; A61K 31/55
USPC ............. 424/451, 464; 514/414, 415, 217.08; 540/602, 609, 612; 548/465, 511
See application file for complete search history.

(56) References Cited

U.S. PATENT DOCUMENTS 5,998,402 A    12/1999  Miller
6,479,535 B1   11/2002  Pickar
(Continued)

FOREIGN PATENT DOCUMENTS

WO    2007/024961 A2    3/2007
WO    2009/012734       1/2009

OTHER PUBLICATIONS

IP.com, Anonymous Disclosure; Process for preparing crystalline 1-[4-(2-azepan-1-yl-ethoxy)-benzyl]-2-(4-hydroxy-phenyl)-3-methyl-1H-indol-5-ol acetic acid Form B, Dec. 2, 2009, IP.com No. IPCOM000190479D.*
Remington's Pharmaceutical Sciences, 18 Sup, th. ed., Mack Publishing Company, Easton, PA, pp. 1635-1636 (1990).
(Continued)

*Primary Examiner* — Jane C Oswecki
(74) *Attorney, Agent, or Firm* — Jeffrey S. Melcher; Manelli Selter PLLC

(57) ABSTRACT

The present invention provides a reliable process for the preparation of polymorphic pure form A of Bazedoxifene x acetate. In addition, the present invention relates to a process of wet granulation of polymorphic pure form A of Bazedoxifene x acetate. The present invention also relates to pharmaceutical compositions comprising polymorphic pure form A of Bazedoxifene x acetate as well as to the use of cyclic ethers for the preparation of such pharmaceutical composition.

9 Claims, 7 Drawing Sheets

(51) Int. Cl.
*A61K 9/16* (2006.01)
*A61K 31/404* (2006.01)
*A61K 31/55* (2006.01)

(56) References Cited

U.S. PATENT DOCUMENTS

| | | | |
|---|---|---|---|
| 7,683,051 B2* | 3/2010 | Demerson et al. | 514/217.08 |
| 7,683,052 B2 | 3/2010 | Ali | |
| 7,771,744 B2* | 8/2010 | Shah et al. | 424/464 |
| 8,183,367 B2* | 5/2012 | Andreella et al. | 540/602 |
| 2007/0048374 A1* | 3/2007 | Shah et al. | 424/464 |
| 2010/0016581 A1 | 1/2010 | Andreella | |
| 2010/0016582 A1 | 1/2010 | Soriato | |

OTHER PUBLICATIONS

"Process for preparing crystalline 1-[4-(2-azepan-1-yl-ethoxy)-benzyl] 2-(4-hydroxy-phenyl)-3-methyl-1Hiindol-5-0)} acetic acid Form B," IP. Com. Journal, IP. Com Inc., West Henrietta, NY, US, Dec. 2, 2009.

Miller, "Design, Synthesis, and Preclinical Characterization of Novel, Highly Selective Indole Estrogens," Journal of Medicinal Chemistry, American Chemical Society, Washington, U.S., vol. 44, No. 11, May 24, 2001.

International Search Report and Written Opinion issued in International Application No. PCT/EP2011/073669, on Feb. 13, 2012.

Jaakko Aaltonen, et. al., "Solid form screening—A Review," European Journal of Pharmacetuics and Biopharmaceutics, 71 (2009) pp. 23-37.

* cited by examiner

METHOD OF PREPARING POLYMORPHIC PURE FORM A OF BAZEDOXIFENE ACETATE

FIELD OF THE INVENTION

The present invention relates to a reliable process for the preparation of polymorphic pure form A of Bazedoxifene x acetate. In addition, the present invention relates to a process of wet granulation of polymorphic pure form A of Bazedoxifene x acetate, wherein conversion to alternate polymorph forms is prevented.

BACKGROUND OF THE INVENTION

Bazedoxifene x acetate, 1-[[4-[2-(Hexahydro-1H-azepin-1-Dethoxy]phenyl]methyl]-2-(4-hydroxyphenyl)-3-methyl-1H-indol-5-ol monoacetate, is a third generation selective estrogen receptor modulator (SERM) that exhibits oestrogen-agonistic tissue-selective activity on the skeletal system and lipid metabolism while also acting as an oestrogen antagonist on breast and uterine tissue. Bazedoxifene x acetate was recently approved in the European Union for the treatment of postmenopausal osteoporosis in women at increased risk of fracture. It is marketed under the brand name Conbriza. The chemical structure of Bazedoxifene x acetate is shown in formula A:

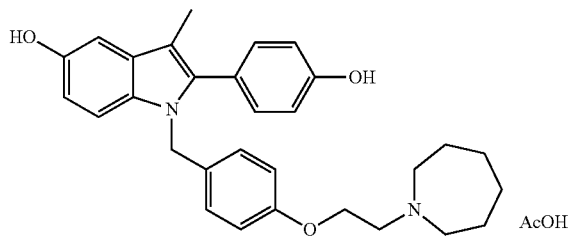

Formula A

Chemical structure of Bazedoxifene x acetate

Polymorphic forms of Bazedoxifene x acetate are disclosed in the prior art. For example, polymorphic form A of Bazedoxifene x acetate and methods of preparing the same are disclosed in U.S. Pat. No. 7,683,051. U.S. Pat. No. 7,683,052 relates to polymorphic form B of Bazedoxifene x acetate and methods of preparing the same. Methods of preparing polymorphic form A of Bazedoxifene x acetate are also described in US 2010/0016581, as well as a method of enhancing the stability of form A. US 2010/0016582 relates to methods of preparing polymorphic form A of Bazedoxifene x acetate.

According to U.S. Pat. No. 7,683,051 and U.S. Pat. No. 7,683,052, table 2, form A of Bazedoxifene x acetate shows higher solubility than form B in both, aqueous and organic solvent systems. Since it is well known that higher solubility can contribute to higher bioavailability, it is assumed that form A shows a higher bioavailability than form B. This is supported by the results of a bioequivalence study (3068A1-129-US) disclosed in the EMEA "assessment report for Conbriza" (EMEA/CHMP/660889/2008). Therefore, form A is preferably used for the preparation of a medicament.

According to U.S. Pat. No. 7,683,051 form A of Bazedoxifene x acetate is prepared by crystallization from alcohols. The crystallization temperature has to be kept at or below 20° C. according to U.S. Pat. No. 7,683,051 in order to obtain form A. At elevated temperatures e.g. at or above 25° C. the proportion of form B is increased according to U.S. Pat. No. 7,683,051. Furthermore, U.S. Pat. No. 7,683,052 describes a process for the preparation of polymorphic form B of Bazedoxifene x acetate by crystallization from alcohols at or above 25° C.

As described in the literature, form B of Bazedoxifene x acetate is the thermodynamically more stable form, whereas form A of Bazedoxifene x acetate is the kinetic (or metastable) form. Therefore, operating conditions and parameters such as crystallization temperature to get pure form A or pure form B of Bazedoxifene x acetate are critical, especially if the crystallization solvent for both polymorphs is identical as disclosed in U.S. Pat. No. 7,683,051 and U.S. Pat. No. 7,683,052.

US 2010/0016581 describes that form A of Bazedoxifene x acetate can easily convert to form B upon contact with a solvent or solvent mixture, for example ethylacetate and ethanol. However, the susceptibility of polymorphic form A of Bazedoxifene x acetate to conversion to alternate polymorph forms considerably affects its suitability for pharmaceutical compositions. US 2010/0016581 therefore suggests to keep polymorphic form A of Bazedoxifene x acetate in dry form in order to prevent undesired polymorphic transition.

In EMEA/CHMP/660889/2008 data for 29 batches of Bazedoxifene x acetate were reported, whereas the level of form II, which corresponds to form B of U.S. Pat. No. 7,683,052 is typically very low. EMEA/CHMP/660889/2008 further states that some of the clinical batches contained low levels of form II (form B of U.S. Pat. No. 7,683,052).

Because polymorphic form A of Bazedoxifene x acetate provides better bioavailability in drug formulations and because conventional preparation techniques require complicated and elaborate control of operating conditions and parameters, there is a need for a new simple and reliable process for the preparation of form A of Bazedoxifene x acetate in polymorphic pure form. The methods of preparing polymorphic pure form A of Bazedoxifene x acetate as described herein helps to meet these and other needs.

SUMMARY OF THE INVENTION

The present invention relates to a process of preparing polymorphic pure form A of Bazedoxifene x acetate. In particular, the present invention relates to a method of preparing polymorphic pure form A of Bazedoxifene x acetate comprising the steps of:
(a) dissolving Bazedoxifene x acetate in a solvent or solvent mixture comprising at least one cyclic ether;
(b) optionally filtering the solution;
(c) stirring the solution in order to initiate crystallization of polymorphic pure form A;
(d) isolating polymorphic pure form A of Bazedoxifene x acetate; and
(e) drying the isolated material.

It was surprisingly found that form A of Bazedoxifene x acetate is obtained in polymorphic pure form by crystallization form cyclic ethers, even at elevated temperatures. In addition, it was found that form A does not convert into form B upon contact with solvents or solvent mixtures comprising at least one cyclic ether.

Therefore, in a further aspect the present invention relates to a process of wet granulation of polymorphic pure form A of Bazedoxifene x acetate, wherein conversion to alternate polymorph forms is prevented. In particular, the present invention relates to a process of wet granulation of polymorphic pure form A of Bazedoxifene x acetate comprising contacting polymorphic pure form A of Bazedoxifene x acetate with a solvent or solvent mixture, which comprises at least one cyclic ether in order to avoid polymorphic interconversions.

The present invention also relates to pharmaceutical compositions comprising polymorphic pure form A of Bazedoxifene x acetate as well as to the use of cyclic ethers for the preparation of such pharmaceutical composition.

DETAILED DESCRIPTION OF THE INVENTION

Figure 1:
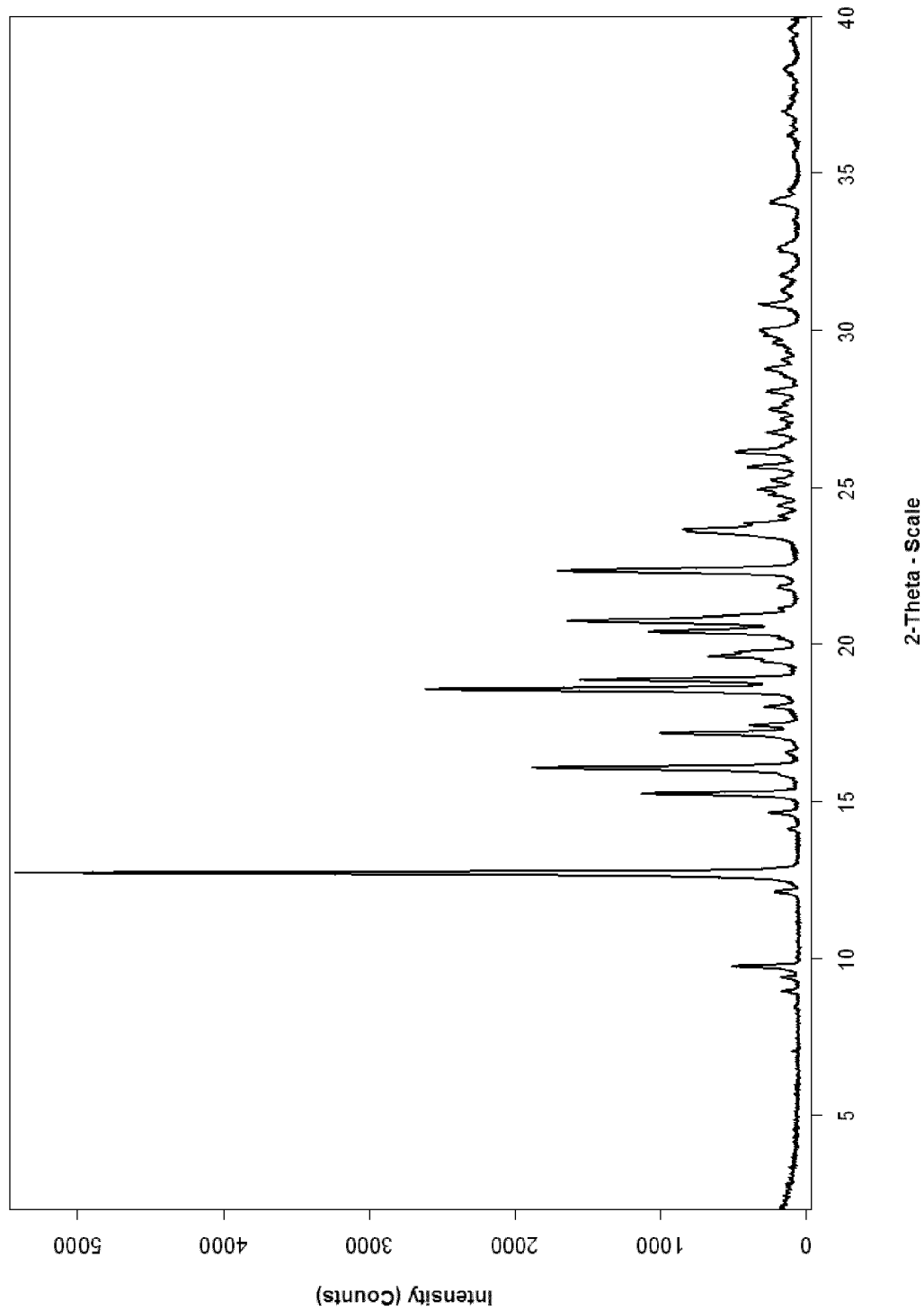
FIG. 1: XRPD pattern of polymorphic pure form A of Bazedoxifene x acetate prepared according to Example 1 of the present invention

The present invention relates to a process of preparing polymorphic pure form A of Bazedoxifene x acetate.

It was surprisingly found that form A of Bazedoxifene x acetate is obtained in polymorphic pure form by crystallization form cyclic ethers, even at elevated temperatures.

Accordingly, the present invention relates to a process of preparing polymorphic pure form A of Bazedoxifene x acetate comprising the steps of:
  (a) dissolving Bazedoxifene x acetate in a solvent or solvent mixture comprising at least one cyclic ether;
  (b) optionally filtering the solution;
  (c) stirring the solution in order to initiate crystallization of polymorphic pure form A;
  (d) isolating polymorphic pure form A of Bazedoxifene x acetate; and
  (e) drying the isolated material.

Bazedoxifene x acetate can be prepared according to U.S. Pat. No. 5,998,402 and U.S. Pat. No. 6,479,535. The preparation of Bazedoxifene x acetate is also described in Miller et al., J. Med. Chem. (2001) 44, 1654-1657. Any form of Bazedoxifene x acetate may be applied in step a) of the above process. Suitable forms are e.g. amorphous Bazedoxifene x acetate, crystalline Bazedoxifene x acetate or mixtures thereof. Suitable crystalline forms are e.g. crystalline form A of U.S. Pat. No. 7,683,051, crystalline form B of U.S. Pat. No. 7,683,052 or crystalline form C described in WO 2009/012734.

In step a) of the above described process Bazedoxifene x acetate is preferably used at a concentration ranging from about 30 to 600 g/l, more preferably from about 40 to 400 g/l and most preferably the concentration used ranges from about 50 to 200 g/l.

The Bazedoxifene x acetate starting material is in admixture with a solvent or a solvent mixture comprising at least one cyclic ether.

As used herein, the term cyclic ether refers to cyclic ethers in general. In a preferred embodiment water-miscible cyclic ethers or mixtures thereof are used, preferably tetrahydrofuran (THF), methyltetrahydrofuran (MTHF) or 1,4-dioxane and mixtures thereof. More preferably, THF is used.

The dissolution step in the process of the present invention may be performed at room temperature. Preferably, the temperature in the dissolution step may range from about 20 to 66° C. when THF is used as solvent, from about 20 to 79° C. when MTHF is used as solvent and from about 20 to 101° C. when 1,4-dioxane is used as solvent.

The terms "room temperature" and "ambient temperature" which may be used interchangeably herein indicate that the applied temperature is not critical and that no exact temperature value has to be kept. Usually, "room temperature" and "ambient temperature" is understood to mean temperatures of about 15° C. to about 25° C. [see European Pharmacopoeia 6.6, 1.2 (2010)].

The obtained solution is optionally filtered in step (b) of the above process in order to remove possible insoluble components.

In step (c) of the above described process the solution is stirred in order to initiate crystallization. The temperature during crystallization is not critical. The solution may be kept in the range from about −20 to 60° C., more preferably from about 0 to 40° C. and most preferably the solution is stirred at ambient temperature without temperature control. Depending on the temperature applied and the concentration used crystallization usually starts within about one hour, more preferably within about 30 minutes and most preferably within about 15 minutes. For example, at ambient temperature crystallization starts within about 10 minutes when using a concentration of about 200 g/l. After the initial crystallization the mixture is further stirred for about 1 to 72 hours, more preferably for about 6 to 48 hours and most preferably for about 12 to 24 hours.

In order to improve the yield, the slurry might be further stirred at decreased temperatures preferably ranging from about −20 to about 20° C., more preferably from about −10 to about 10° C. and most preferably from about −5 to about 5° C. for a time preferably ranging from about 1 to 24 hours, more preferably from about 1 to 12 hours and most preferably from about 1 to 6 hours.

In step d) of the above process the solid is isolated, whereas any conventional method such as filtration, centrifugation or evaporation of the solvent may be applied.

Drying in step e) of the present process may be performed under vacuum at a temperature preferably ranging from about 20 to about 80° C., more preferably from about 20 to about 60° C. and most preferably from about 30 to about 50° C. Drying is preferably conducted for about 1 to about 72 hours, more preferably for about 1 to about 48 hours and most preferably for about 1 to about 24 hours.

As described herein, it was surprisingly found that form A of Bazedoxifene x acetate was obtained in polymorphic pure form by crystallization from cyclic ethers even at elevated temperatures. Accordingly, polymorphic pure form A of Bazedoxifene x acetate was obtained by crystallization from THF, whereas the crystallization was performed at ambient conditions without control of the crystallization temperature (see Example 1). In contrast, crystallization from ethanol at ambient conditions without control of the crystallization temperature resulted in form B of Bazedoxifene x acetate (see Example 2).

In Example 3, further crystallization experiments with different solvents and without controlling the crystallization temperature were performed, confirming that crystallizations from cyclic ethers such as THF, MTHF and 1,4-dioxane resulted in pure polymorphic form A. Crystallizations from alcohols, esters and acetonitrile resulted in form B of Bazedoxifene x acetate. Crystallizations from ketones resulted either in a mixture of form A and form B or in pure form B.

Crystallization of Bazedoxifene x acetate from cyclic ethers like THF, MTHF and 1,4-dioxane results in polymorphic pure form A and is not critical with respect to crystallization temperature.

Therefore, the present invention provides a reliable process for the preparation of polymorphic pure form A of Bazedoxifene x acetate without the need of temperature control.

The polymorphic pure form A of Bazedoxifene x acetate prepared according to the method of the present invention comprises essentially pure polymorph A containing at least about 95%, preferably at least 97%, more preferably at least 99%, and most preferably at least 99.9% of Bazedoxifene polymorph A, when measured by XRPD or DSC.

Accordingly, the present invention further relates to polymorphic pure form A of Bazedoxifene x acetate with a polymorphic purity of at least about 95%, preferably at least 97%, more preferably at least 99%, and most preferably at least 99.9% of Bazedoxifene x acetate polymorph A. The present invention also relates to the use of cyclic ethers for the preparation of crystalline form A of Bazedoxifene x acetate in polymorphic pure form.

Figure 3:
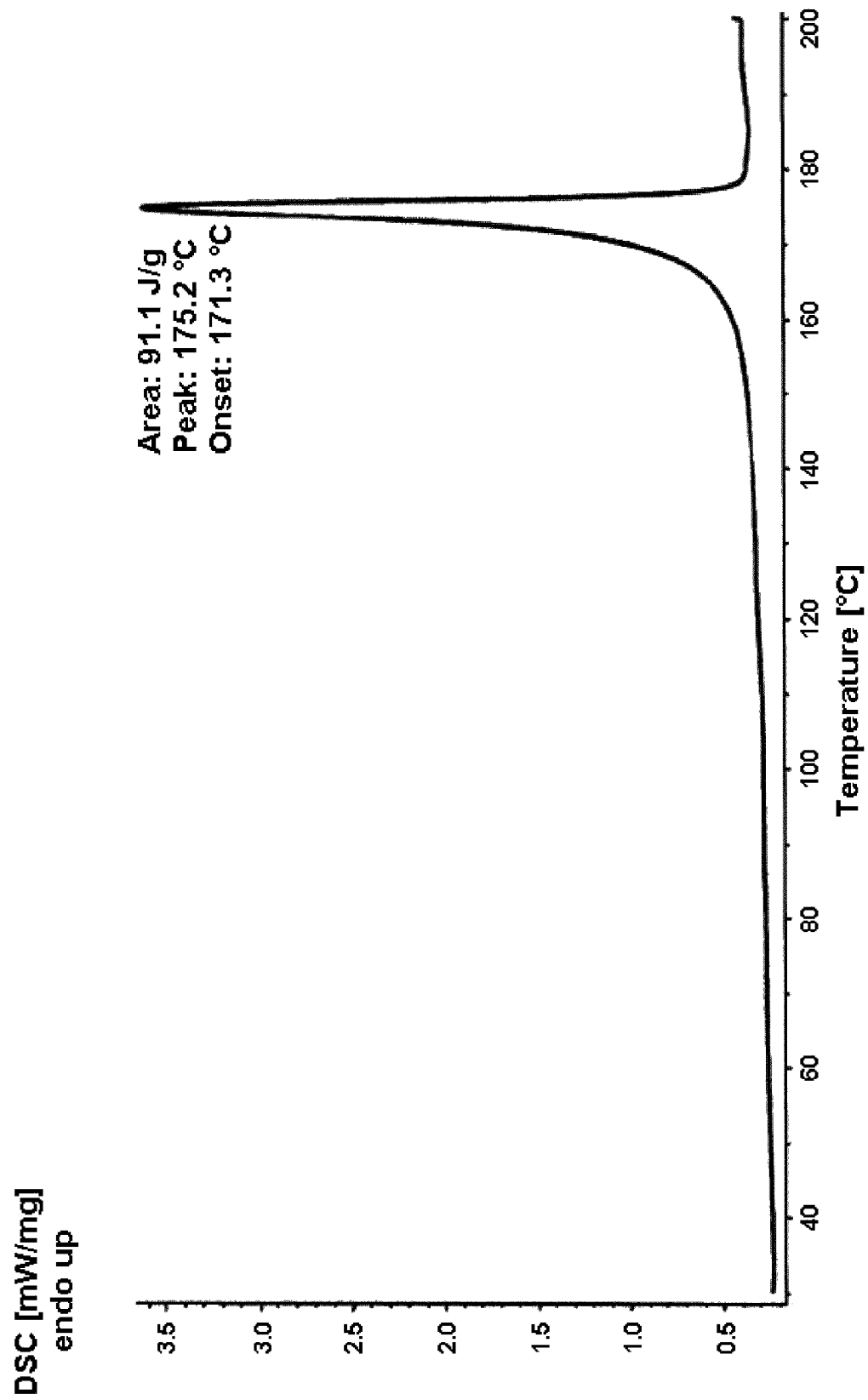
FIG. 3: DSC curve of polymorphic pure form A of Bazedoxifene x acetate prepared according to Example 1 of the present invention

In a preferred embodiment, polymorph A of Bazedoxifene x acetate of the present invention is obtained in polymorphic pure form according to the process of the present invention, whereas the polymorphic purity is defined by the DSC trace shown in FIG. 3. Form A has a lower melting point than form B. Therefore the presence of a second, higher melting endotherm in a DSC curve of form A is indicative for the presence of form B in form A. According to US 2010/0016581 detection of form B in form A is viable down to below 0.1% form B in form A by using DSC.

Figure 6:
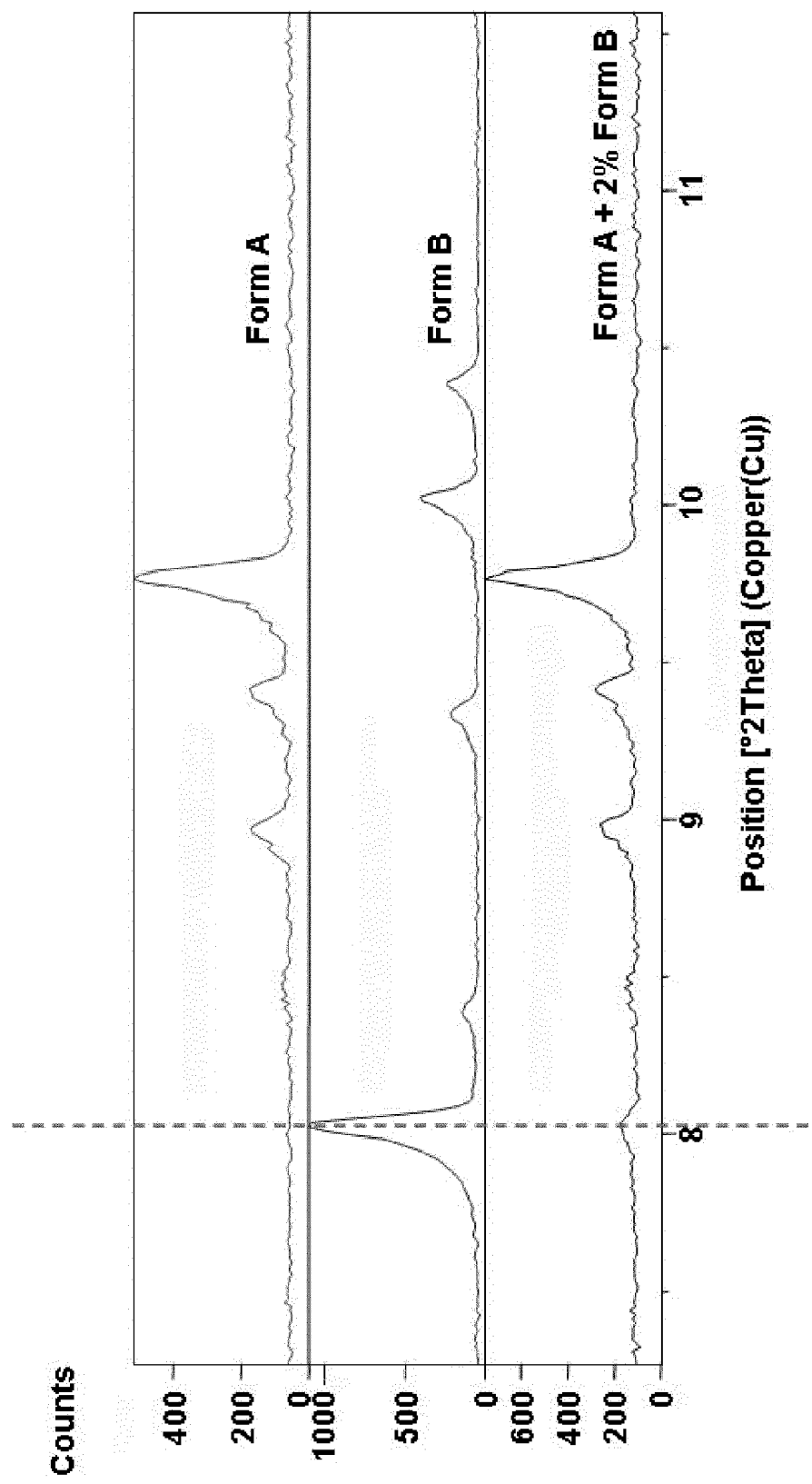
FIG. 6: Overlay XRPD patterns from about 7.5 to 11.5° 2-theta of polymorphic pure form A, polymorphic pure form B and form A with 2 w % form B
Figure 7:
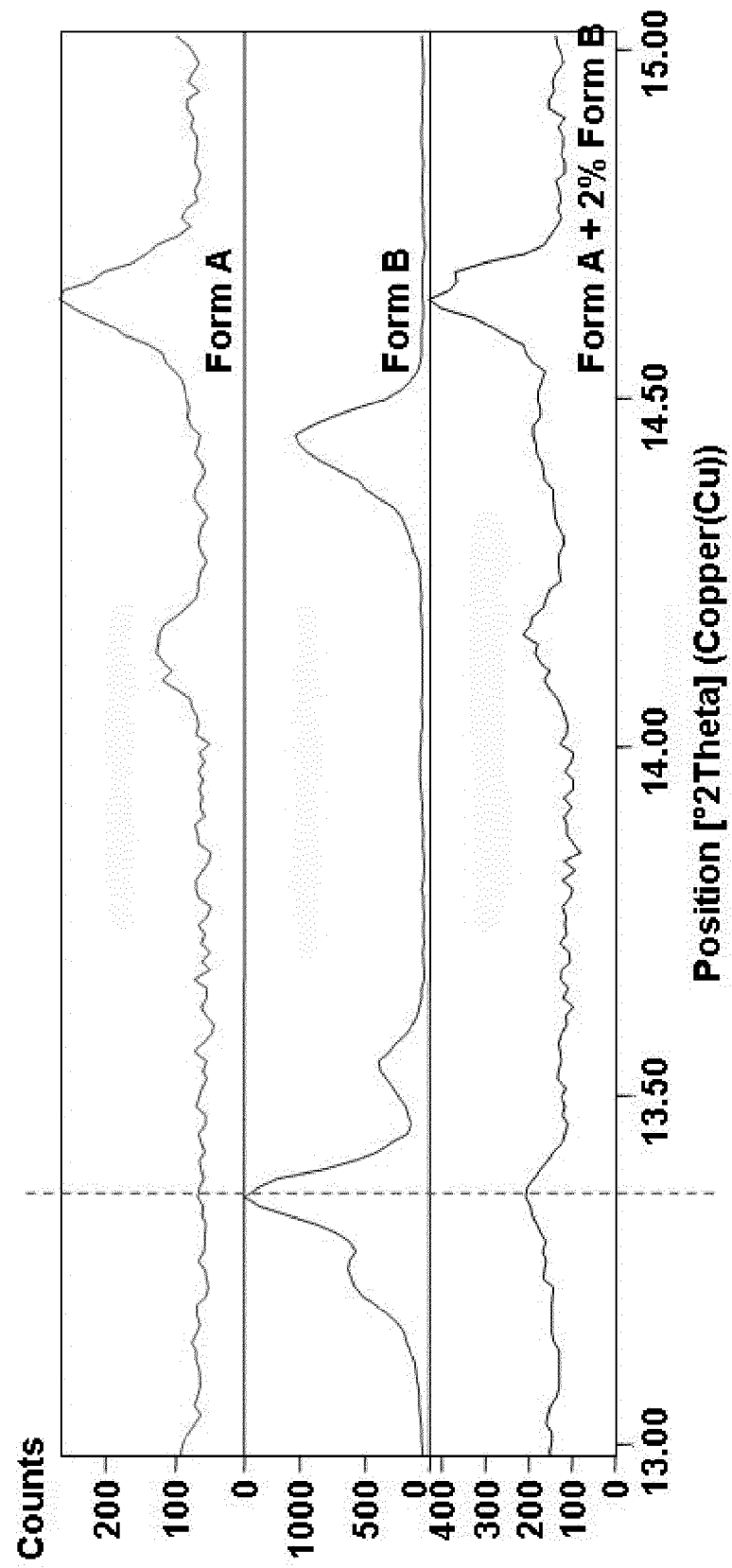
FIG. 7: Overlay XRPD patterns from about 13.0 to 15.0° 2-theta of polymorphic pure form A, polymorphic pure form B and form A with 2 w % form B

The polymorphic purity of form A by XRPD is further verified by the absence of form B peaks at 8.0±0.2° 2-theta and at 13.4±0.2° 2-theta (see FIGS. 6 and 7). The limit of detection of form B in form A via this method was determined to be about 2 to 3 w %.

According to US 2010/0016581 form A of Bazedoxifene x acetate can easily convert to form B upon contact with a solvent or solvent mixture, for example ethyl acetate and ethanol. Therefore, US 2010/0016581 suggests to keep polymorphic form A of Bazedoxifene x acetate in dry form in order to prevent undesired polymorphic transition.

Surprisingly, polymorphic form A of Bazedoxifene x acetate remains stable when slurrying it in cyclic ethers such as THF, MTHF and 1,4-dioxane at 30° C. overnight, whereas a transformation to form B occurs when slurrying form A in methanol. In addition, form A partially converts to form B when stirring a suspension of form A in ethanol at 30° C. overnight (see Example 4).

Therefore, the finding that form A does not convert to form B upon contact with a solvent or solvent mixture as described in accordance with the present invention, i.e. solvents or solvent mixtures comprising cyclic ethers even at elevated temperatures, allows for the first time the preparation of pharmaceutical composition comprising polymorphic pure form A of Bazedoxifene x acetate by wet granulation.

In particular, wet granulation is one of the most prevalent methods and is also the preferred granulation method in the context of pharmaceutical compositions comprising polymorphic pure form A of Bazedoxifene x acetate. Wet granulation methods can be used where the flow properties of a compound such as an active pharmaceutical ingredient are poor which result in content uniformity issues when formulated as a dry blend. It is commonly used to improve the processing characteristics of a powder blend, including improved flowability, content uniformity and more uniform particle size.

Therefore, in a further aspect the present invention relates to a process of wet granulation of polymorphic pure form A of Bazedoxifene x acetate, wherein conversion to alternate polymorph forms is prevented. In particular, the present invention relates to a process of wet granulation of polymorphic pure form A of Bazedoxifene x acetate using a solvent or solvent mixture, which comprises at least one cyclic ether in order to avoid polymorphic interconversions.

In particular, the present invention relates to a method of preparing a pharmaceutical composition comprising polymorphic pure form A of Bazedoxifene x acetate, said method comprising:

(a) contacting polymorphic pure form A Bazedoxifene x acetate with a solvent or solvent mixture comprising at least one cyclic ether to form a wet granulation; and (b) drying the wet granulation to form a pharmaceutical composition.

In a preferred embodiment the method further comprises the step of encapsulating or tabletting the pharmaceutical composition obtained in step (b).

The method of wet granulation of polymorphic pure form A of Bazedoxifene x acetate according to the present invention comprises a step of preparation of a wet phase comprising polymorphic pure form A of Bazedoxifene x acetate, wherein form A of Bazedoxifene x acetate is contacted with a solvent or solvent mixture, which comprises at least one cyclic ether.

In wet granulation at least one of the ingredients may be mixed or contacted with liquid and further processed to provide aggregates, the liquid may be partially or completely removed, by for example drying and optionally more of the same ingredients or other excipients may be further added and solid dosage forms manufactured. Capsules containing the solid composition may be made of gelatin or other encapsulating material.

Wet granulated formulations may need to have an agent called a "binder", which, in contact with water, swells or starts dissolving, forming a gel-like consistency. Traditionally, starch, starch paste, gelatin, and cellulosics such as hydroxypropylmethyl cellulose, hydroxyethyl cellulose, hydroxypropyl cellulose, polyvinyl pyrrolidone are used as binding agents in wet granulation formulations. (See, Remington's Pharmaceutical Sciences, 18.sup.th ed., Mack Publishing Company: Easton, Pa., 1635-1636 (1990)). Microcrystalline cellulose, such as Avicel PH101, may be employed as a binder or compression aid in compositions prepared by dry granulation formulation, but microcrystalline cellulose functions primarily as a bulking agent in wet granulation formulations because the microcrystalline cellulose loses much of its binding properties upon wetting. In addition, lubricants may be used, such as magnesium stearate, calcium stearate, stearic acid, surface active agents such as sodium lauryl sulfate, propylene glycol, sodium dodecane sulfonate, sodium oleate sulfonate, and sodium laurate mixed with stearates and talc, sodium stearyl fumerate, and other known lubricants.

The present invention also relates to pharmaceutical compositions comprising the Bazedoxifene x acetate polymorph A prepared according to the process of the present invention. Formulations include therapeutically effective amounts that can be given in daily dose ranging from 0.1 mg to 200 mg to a person in need.

Such dosages can be administered in any manner that facilitates the compound's entry into the blood stream including orally, via implantates, parenterally (including intravenous, intraperitoneal, and subcutaneous injection) and transdermally.

In a further aspect, the present invention relates to a pharmaceutical composition comprising polymorphic pure form A of Bazedoxifene x acetate substantially free of cyclic ethers. In a preferred embodiment, such pharmaceutical composition is substantially free of cyclic ethers. Preferably, such pharmaceutical composition comprises less than 10.0% cyclic ethers, more preferably less than 1.0% cyclic ethers, particularly more preferably less than 0.5% cyclic ethers and most preferably less than 0.1% cyclic ethers.

Oral formulations containing the polymorph according to the process of the present invention comprise any conventially used oral forms, including tablets, capsules, buccal forms, troches, lozenges and oral liquids, suspensions or solutions. Capsules or tablets may also be combined with mixtures of other active compounds or inert fillers and/or diluents such as the pharmaceutically acceptable starches, sugars, artificial sweetening agents, powdered cellulose, gelatins, gums etc.

Tablet formulations can be made by conventional compression, wet granulation, or dry granulation methods and utilization of pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride and powdered sugar.

Oral formulations used herein can utilize standard delay or time release formulations or spansules. Example excipient systems suitable for preparing formulations of the present polymorph include one or more fillers, disintegrants and lubricants.

Preferred formulations of the polymorph prepared according to the process of the invention are disclosed for example in US 2007/0048347.

Other objects, features, advantages and aspects of the present invention will become apparent to those of skilled in the art from the description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and from reading the other parts of the present disclosure.

EXAMPLES

XRPD patterns were obtained with an X'Pert PRO diffractometer (PANalytical, Almelo, The Netherlands) equipped with a theta/theta coupled goniometer in transmission geometry, programmable XYZ stage with well plate holder, Cu—K$\alpha_{1,2}$ radiation source (wavelength 0.15419 nm) with a focusing mirror, a 0.5° divergence slit, a 0.02° soller slit collimator and a 1° anti-scattering slit on the incident beam side, a 2 mm anti-scattering slit, a 0.02° soller slit collimator and a Nickel filter on the diffracted beam side and a solid state PIXcel detector. The patterns were recorded at a tube voltage of 40 kV, tube current of 40 mA, applying a stepsize of 0.013° 2-theta with 40 s per step in the angular range of 2° to 40° 2-theta. Diffractograms of mixtures of Form A with 2% Form B in FIGS. 6 and 7 were recorded with 80 s per step.

Differential scanning calorimetry (DSC) was performed with a DSC 7 (Perkin-Elmer, Norwalk, Conn., USA) using a Pyris 2.0 software. 2.057 mg (form A) respectively 3.239 mg (form B) sample (using a UM3 ultramicrobalance, Mettler, Greifensee, CH) were weighed into an Al-pan (25 µl) and sealed with a cover. Dry nitrogen was used as the purge gas (purge: 20 ml/min).

Example 1

Crystallization of Bazedoxifene x Acetate from THF

A solution of 4.0 g Bazedoxifene x acetate (amorphous starting material) in 20 ml THF was stirred at ambient temperature whereas crystallization started within 10 minutes. The mixture was stirred for 19 hours, before the solid was collected by filtration. After washing with THF the material was dried at 40° C. under vacuum for about 4 hours. The thus obtained material was investigated by XRPD and DSC and identified as polymorphic pure form A.

The material prepared according to Example 1 has an XRPD-pattern as displayed in FIG. 1. Due to the missing peaks at 8.0 and 13.4° 2-theta the material obtained from Example 1 is proven to be form A of Bazedoxifene x acetate in polymorphic pure form.

In addition the material prepared according to Example 1 has a DSC curve as displayed in FIG. 3. As can be seen from FIG. 3 the DSC curve shows a single endotherm with a peak maximum at about 175.2° C. and a heat of fusion of about 91.1 J/g, which corresponds to form A of Bazedoxifene x acetate. Due to the lack of a second, higher endotherm at about 178.4° C. the material is again proven to be polymorphic pure.

Example 2

Crystallization of Bazedoxifene x Acetate from Ethanol

A solution of 421 mg Bazedoxifene x acetate (amorphous starting material) in 2 ml ethanol was stirred at ambient temperature, whereas crystallization started within 1 minute. The mixture was stirred for 17 hours, before the solid was collected by filtration. After washing with ethanol the material was dried at 40° C. under vacuum for about 8.5 hours. The thus obtained material was investigated by XRPD and DSC and identified as crystalline form B.

Figure 2:
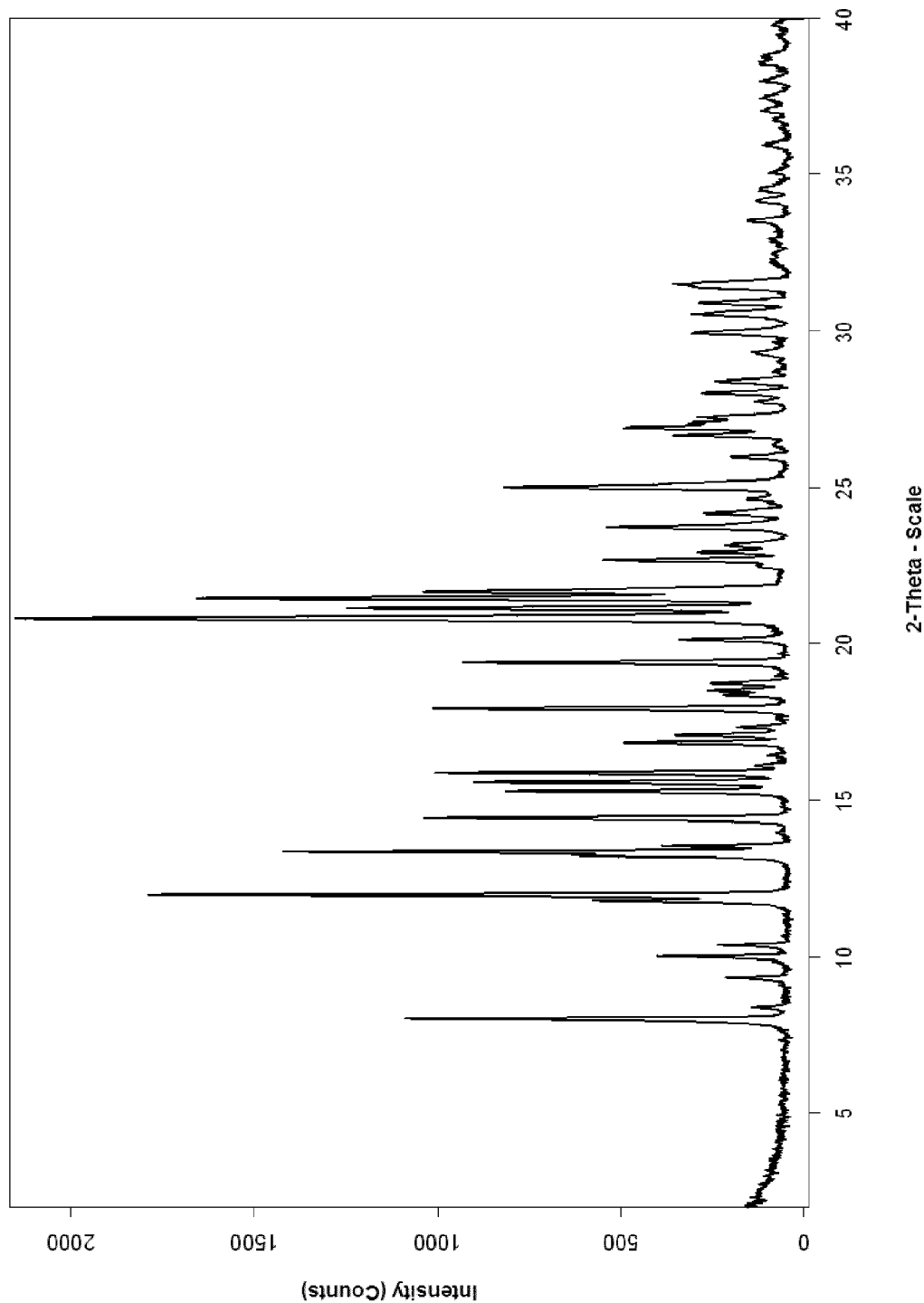
FIG. 2: XRPD pattern of polymorphic pure form B of Bazedoxifene x acetate prepared according to Example 2 of the present invention

The material prepared according to Example 2 has an XRPD-pattern as displayed in FIG. 2. Table 1 compares the peak positions of polymorphic pure form A obtained from Example 1 and polymorphic pure form B obtained from Example 2.

TABLE 1

Peak positions of form A and form B Position (°2-theta)

| form A from Example 1 | form B from Example 2 |
|---|---|
|  | 8.0 |
| 9.8 |  |
|  | 10.0 |
|  | 12.0 |
| 12.7 |  |
|  | 13.4 |
|  | 14.4 |
| 15.3 | 15.3 |
|  | 15.6 |
| 16.1 | 15.9 |
|  | 16.8 |
| 17.2 |  |
|  | 17.9 |
| 18.6 |  |
| 18.9 |  |
| 19.6 | 19.4 |
| 20.4 |  |
| 20.8 | 20.8 |
|  | 21.1 |
|  | 21.5 |
|  | 21.7 |
| 22.3 |  |
|  | 22.7 |
| 23.7 | 23.7 |
|  | 25.0 |
| 26.1 |  |
|  | 26.9 |

Figure 4:
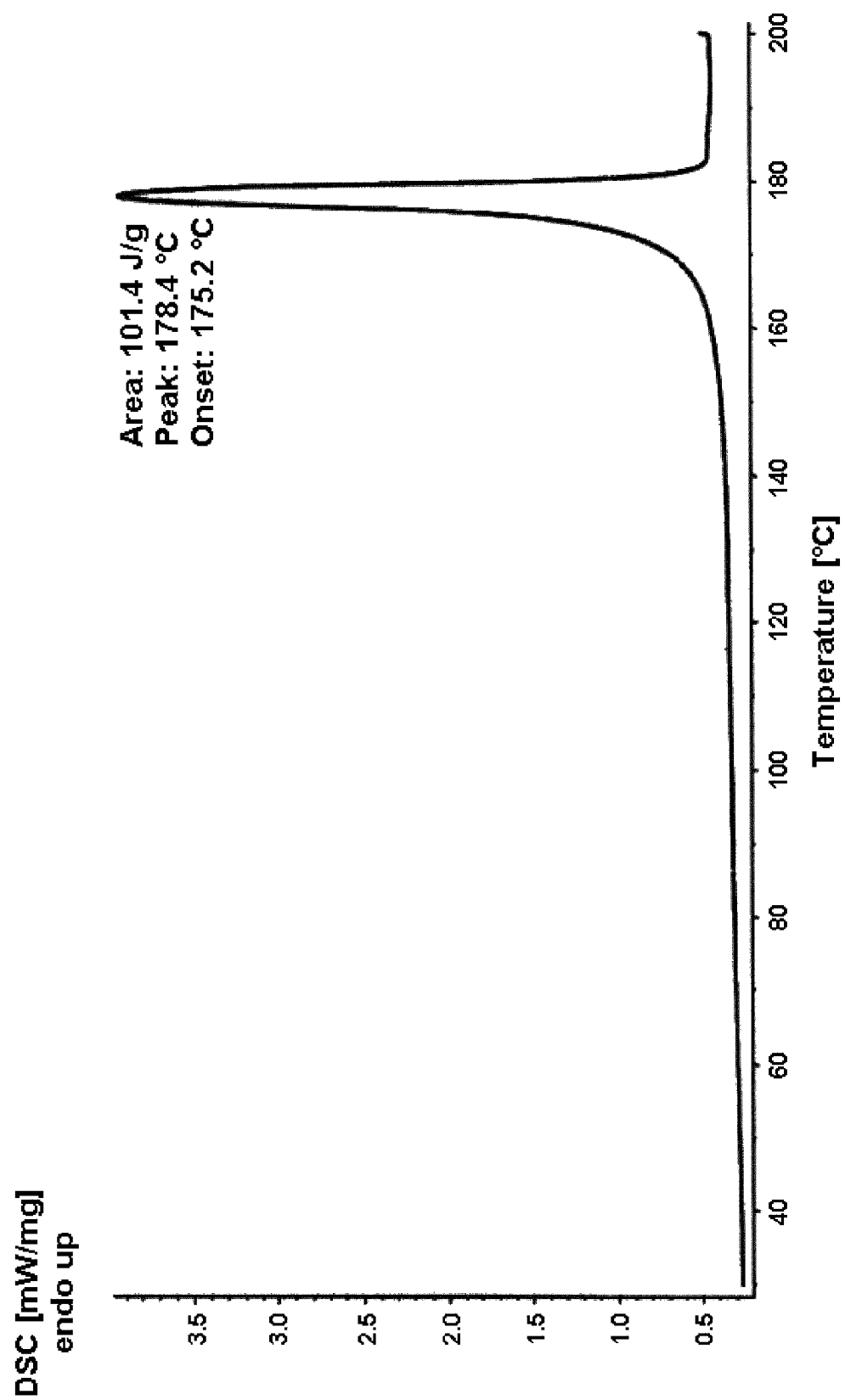
FIG. 4: DSC curve of polymorphic pure form B of Bazedoxifene x acetate prepared according to Example 2 of the present invention
Figure 5:
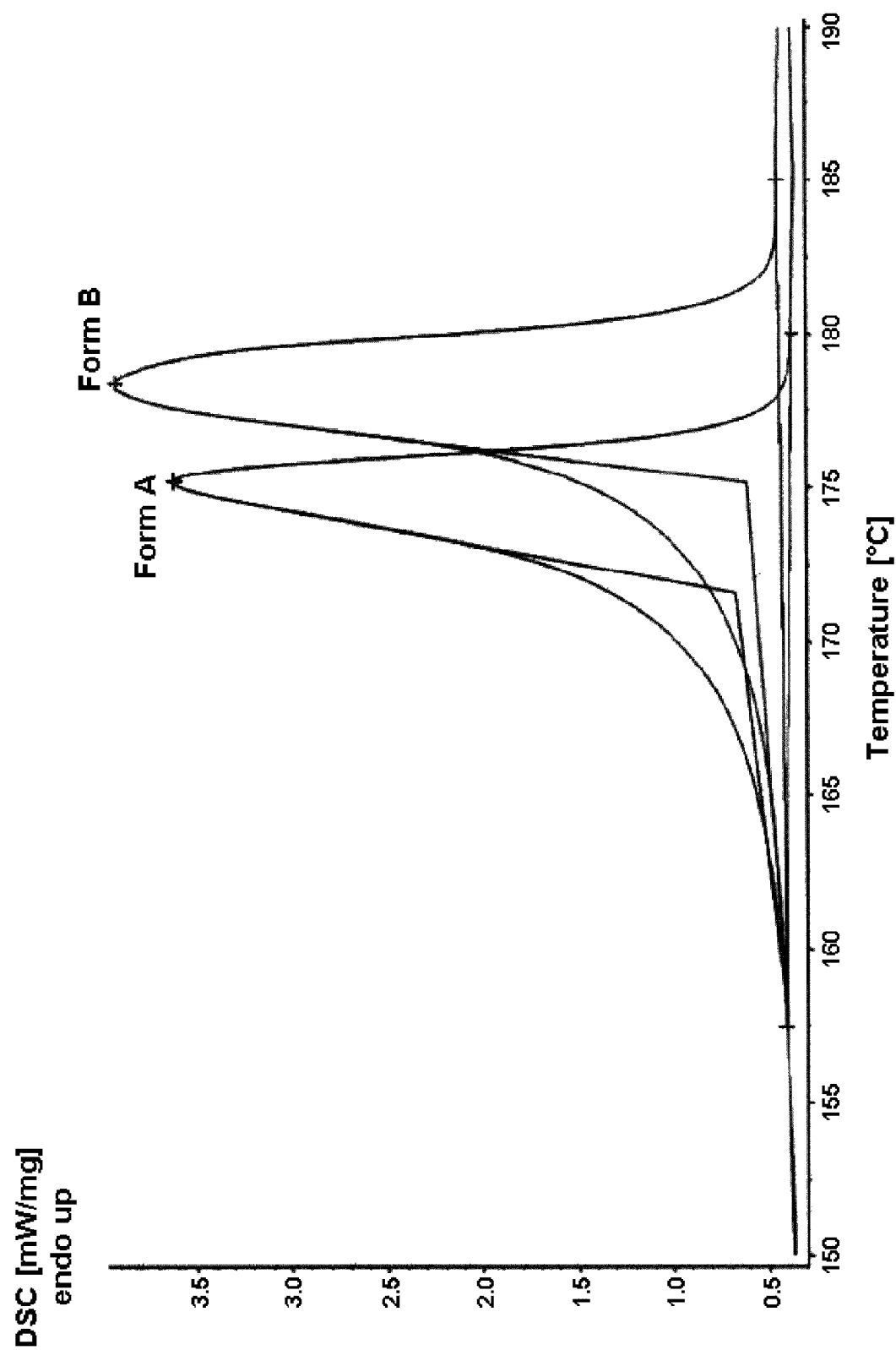
FIG. 5: Overlay DSC curves of polymorphic pure form A of Bazedoxifene x acetate prepared according to Example 1 of the present invention and polymorphic pure form B of Bazedoxifene x acetate prepared according to Example 2 of the present invention

In addition the material prepared according to Example 2 has a DSC curve as displayed in FIG. 4. As can be seen from FIG. 4 the DSC curve shows a single endotherm with a peak maximum at about 178.4° C. and a heat of fusion of about 101.4 J/g, which corresponds to form B of Bazedoxifene x acetate.

Example 3

Bazedoxifene x Acetate—Solvent Screening

Starting from amorphous Bazedoxifene x acetate, crystallization experiments with different solvents were performed without controlling the crystallization temperature. Solutions of Bazedoxifene x acetate in the solvents listed in table 2 were prepared either at ambient temperature or by heating to reflux where necessary. After crystallization the materials were isolated by filtration, dried and investigated by FTIR. In some cases additional XRPD-patterns were collected in order to unambiguously determine the solid state phases. The results are summarized in table 2.

TABLE 2

Results of solvent screening experiments

| Solvent | Solubility | Form |
|---|---|---|
| tetrahydrofurane | ambient temperature | A |
| methyltetrahydrofurane | ambient temperature | A |
| 1,4-dioxane | ambient temperature | A |
| methanol | ambient temperature | B |
| ethanol | ambient temperature | B |
| 1-propanol | ambient temperature | B |
| isopropanol | reflux | B |
| 1-butanol | ambient temperature | B |
| 2-butanol | reflux | B |
| isobutanol | reflux | B |
| n-amyl alcohol | ambient temperature | B |
| isoamyl alcohol | reflux | B |
| ethylene glycol | ambient temperature | B |
| ethylmethylketone | reflux | A + B |
| isobutylmethylketone | reflux | B |
| methylacetate | reflux | B |
| ethylacetate | reflux | B |
| acetonitrile | reflux | B |

Example 4

Stability of Bazedoxifene x Acetate form A in Different Solvents

The effect of different solvents on the transformation of Bazedoxifene x acetate form A to form B was investigated. Bazedoxifene x acetate form A prepared according to Example 1 was slurried in different solvents at 30° C. overnight. Thereafter the suspensions were cooled to 0° C. (except the suspension with 1,4-dioxane was cooled to 25° C.) and kept at the same temperature for additional 2 hours. The solids were collected by filtration, dried at room temperature under vacuum overnight and analyzed by DSC. The results are displayed in table 3.

TABLE 3

Results of stability study in different solvents

| Solvent | c [mg/ml] | Form |
|---|---|---|
| methanol | 100 | B |
| ethanol | 50 | A + trace B |
| THF | 100 | A |
| 1,4-dioxane | 100 | A |
| Methyl-THF | 50 | A |

As can be seen from table 3 form A transforms to form B in methanol. In ethanol a trace of form B was detected, whereas form A undergoes no transition in THF, MTHF and 1,4-dioxane.

The invention claimed is:

1. A method for the preparation of polymorphic pure form A of Bazedoxifene x acetate comprising the steps of:
   (a) dissolving Bazedoxifene x acetate in a solvent or solvent mixture comprising at least one cyclic ether to provide a solution comprising Bazedoxifene x acetate;
   (b) optionally filtering the solution;
   (c) stirring the solution in order to initiate crystallization of polymorphic form A;
   (d) isolating polymorphic form A of Bazedoxifene x acetate; and
   (e) drying the isolated polymorphic form A of Bazedoxifene x acetate.

2. The method according to claim 1, wherein the cyclic ether is tetrahydrofuran, methyltetrahydrofuran and 1,4-dioxane.

3. The method according to claim 1, wherein the cyclic ether is tetrahydrofuran.

4. A method of using at least one cyclic ethers for the crystallization of polymorphic pure form A of Bazedoxifene x acetate.

5. A method of using at least one cyclic ethers in a process of wet granulation for the preparation of pharmaceutical compositions comprising polymorphic pure form A of Bazedoxifene x acetate as pharmaceutical active ingredient.

6. A method of preparing a pharmaceutical composition comprising polymorphic pure form A of Bazedoxifene x acetate, said method comprising:
   (a) contacting polymorphic pure form A Bazedoxifene x acetate with a solvent or solvent mixture comprising at least one cyclic ether to form a wet granulation; and
   (b) drying the wet granulation to form the pharmaceutical composition comprising polymorphic pure form A of Bazedoxifene x acetate.

7. The method of claim 6, further comprising the step of encapsulating or tabletting the pharmaceutical composition obtained in step (b).

8. A pharmaceutical composition obtainable or obtained by the method of claim 6, said pharmaceutical composition being substantially free of cyclic ethers.

9. The pharmaceutical composition of claim 8, comprising less than 0.5% cyclic ethers based on the total weight of the pharmaceutical composition.

* * * * *